United States Patent
Tanabe et al.

(10) Patent No.: US 8,639,078 B2
(45) Date of Patent: Jan. 28, 2014

(54) OPTICAL FIBER MANUFACTURING METHOD, OPTICAL FIBER AND ENDOSCOPE

(71) Applicant: Olympus Corporation, Tokyo (JP)

(72) Inventors: Makoto Tanabe, Hachioji (JP); Hiroki Takagi, Fujimi (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/850,549

(22) Filed: Mar. 26, 2013

(65) Prior Publication Data

US 2013/0259436 A1    Oct. 3, 2013

Related U.S. Application Data

(63) Continuation of application No. PCT/JP2012/081973, filed on Dec. 10, 2012.

(30) Foreign Application Priority Data

Dec. 19, 2011   (JP) .................................. 2011-277355

(51) Int. Cl.
| | |
|---|---|
| *G02B 6/02* | (2006.01) |
| *G02B 6/06* | (2006.01) |
| *C03C 13/04* | (2006.01) |
| *C03B 37/023* | (2006.01) |

(52) U.S. Cl.
USPC ................ 385/123; 385/117; 501/37; 65/385

(58) Field of Classification Search
USPC ......................... 385/117, 123; 65/385; 501/37
See application file for complete search history.

(56) References Cited

U.S. PATENT DOCUMENTS

2004/0223715 A1 * 11/2004 Benoit et al. .................. 385/123

FOREIGN PATENT DOCUMENTS

| JP | 01-215738 | 8/1989 |
|---|---|---|
| JP | 09-040437 | 2/1997 |
| JP | 2002-529357 | 9/2002 |
| WO | WO 00/10932 | 3/2000 |
| WO | WO 00/27773 | 5/2000 |

* cited by examiner

*Primary Examiner* — Ryan Lepisto
*Assistant Examiner* — Erin Chiem
(74) *Attorney, Agent, or Firm* — Scully, Scott, Murphy & Presser, P.C.

(57) ABSTRACT

Provided is a method for manufacturing an optical fiber that is inserted into an insertion portion of an endoscope and guides light, wherein inside an upright fiber drawing furnace, inside a hollow clad tube including a clad glass having a viscosity η1 of 5.0<Log η1<7.0 at a temperature at which a viscosity η2 of a core glass becomes Log η2=3.5, the core glass in a fluidized state runs down by gravity, whereby the core glass and the clad glass are integrated.

8 Claims, 4 Drawing Sheets

OPTICAL FIBER MANUFACTURING METHOD, OPTICAL FIBER AND ENDOSCOPE

CROSS REFERENCE TO RELATED APPLICATION

This application is a continuation application of PCT/JP2012/081973 filed on Dec. 10, 2012 and claims benefit of Japanese Application No. 2011-277355 filed in Japan on Dec. 19, 2011, the entire contents of which are incorporated herein by this reference.

BACKGROUND OF THE INVENTION

1. Field of the Invention

Embodiments of the present invention relate to a method for manufacturing an optical fiber that is inserted into an insertion portion of an endoscope and guides light, the optical fiber, and an endoscope including the optical fiber.

2. Description of the Related Art

Medical endoscopes need to illuminate an object in order to observe the inside of a dark body cavity. Therefore, a light guide is used to guide light generated by a light source apparatus to an illumination portion disposed in a distal end portion of an insertion portion of the respective endoscopes.

A light guide has a configuration in which numerous optical fibers are bundled. As illustrated in FIG. 1, each of the respective optical fibers 10 (with an outer diameter $\phi F$) includes a core 11 (with an outer diameter $\phi C$) that transmits light and a clad 12 that is provided on an outer circumferential portion of the core 11 and reflects light to prevent the light from leaking to the outside from a side face of the core. For the core 11, a high-refractive index glass is used, and for the clad 12, a glass with a refractive index that is lower than that of the core 11 is used.

As an example of optical fiber manufacturing methods, Japanese Patent Application Laid-Open Publication No. 1-215738 discloses a method for manufacturing an optical fiber for optical communications using a rod-in-tube method. In a rod-in-tube method, melt-spinning, what is called "fiber drawing", is performed with a rod-like glass, which becomes a core, inserted into a tubular glass, which becomes a clad, in an inner portion of a heating furnace.

Here, optical fibers for endoscopes and optical fibers for optical communications both have a function that guides light and thus are similar to each other in their basic parts. However, while optical fibers for optical communications each convey light with a predetermined narrow range of wavelengths over a long distance of several kilometers or more, optical fibers for endoscopes need to guide a large amount of light with a broad range of wavelengths, i.e., visible light, although the optical fibers for endoscopes guide such large amount of light over only a short distance of several meters. Thus, although a structure of optical fibers for endoscopes and a method for manufacturing the same are similar in basic part to, but largely different in, e.g., manufacturing conditions from, a structure of optical fibers for optical communications and a method for manufacturing the same.

SUMMARY OF THE INVENTION

An embodiment of the present invention provides a method for manufacturing an optical fiber that is inserted into an insertion portion of an endoscope and guides light, wherein in an inner portion of an upright fiber drawing furnace used in an rod-in-tube method, in an inner portion of a hollow tube including a clad glass having a viscosity $\eta 1$ of $5.0 < \text{Log } \eta 1 < 7.0$ at a temperature at which a viscosity $\eta 2$ of a core glass becomes $\text{Log } \eta 2 = 3.5$, the core glass in a fluidized state runs down by gravity, whereby the core glass and the clad glass are integrated.

Another embodiment of the present invention provides an optical fiber that is inserted into an insertion portion of an endoscope and guides light, wherein a viscosity $\eta 1$ of a clad glass at a temperature at which a viscosity $\eta 2$ of a core glass becomes $\text{Log } \eta 2 = 3.5$ is $5.0 < \text{Log } \eta 1 < 7.0$.

Yet another embodiment of the present invention provides an endoscope including an optical fiber that is inserted into an insertion portion and guides light, wherein a viscosity $\eta 1$ of a clad glass at a temperature at which a viscosity $\eta 2$ of a core glass becomes $\text{Log } \eta 2 = 3.5$ is $5.0 < \text{Log } \eta 1 < 7.0$.

DETAILED DESCRIPTION OF THE PREFERRED EMBODIMENTS

Figure 1:
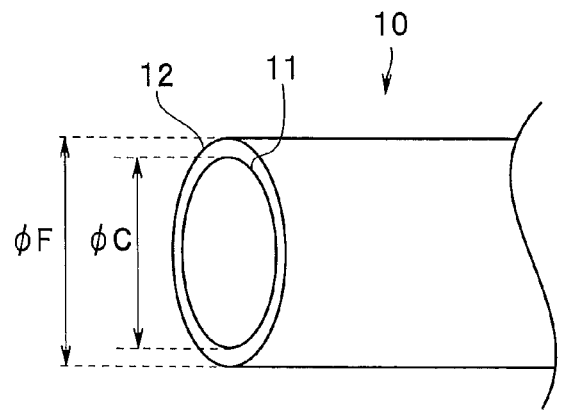
FIG. 1 is a diagram for describing a structure of an optical fiber.
Figure 2:
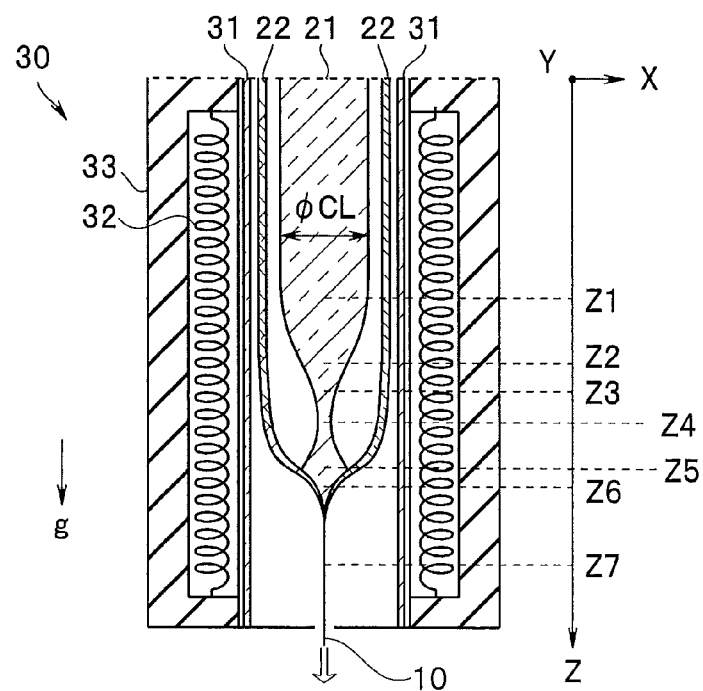
FIG. 2 is a schematic cross-sectional diagram for describing a method for manufacturing an optical fiber according to a rod-in-tube method using a fiber drawing furnace according to an embodiment.

As illustrated in FIG. 2, an optical fiber 10 according to an embodiment is obtained as a result of a vertically held, elongated core rod 21 including a core glass inserted into a center of a hollow portion of a vertically-held, elongated clad tube 22 including a clad glass being heated and subjected to "fiber drawing" under downward tension in an inner portion of an upright fiber drawing furnace 30.

In the fiber drawing furnace 30, a heater 32 and a heat-insulating material 33 are disposed so as to surround a central furnace tube 31, which provides a heating space. An inner portion of the furnace tube 31 is designed so that the temperature increases toward the lower side from the upper side.

Hereinafter, as illustrated in FIG. 2, positions Z in the inner portion of the fiber drawing furnace 30 are indicated by values in a Z-axis coordinate in which an upper portion of the fiber drawing furnace 30 is an origin thereof and a Z-axis is an axis with its value increasing toward the lower side (in a gravity direction g). Here, FIG. 2 is a schematic diagram for description in which, e.g., shapes and/or sizes of components are different from those of actual ones.

In the optical fiber 10, the core glass (core rod 21) enters a fluidized state at a temperature lower than that of the clad glass (clad tube 22). Thus, as illustrated in FIG. 2, the core rod 21 starts deformation and fluidization at Z1, and enters a fluidized state and vertically runs down by gravity at Z2. The core glass (core rod 21) that has run down is integrated with the clad tube 22 at Z2. Note that the clad glass (clad tube 22) starts deformation and fluidization at Z3 and a diameter thereof starts decreasing.

Here, a diameter φCL of the core glass (core rod 21) that has entered a fluidized state and started running down at Z2 gradually decreases toward the lower side, but the core glass (core rod 21) is received by the clad tube 22 that is not in a fluidized state at Z5 and thus exhibits a minimum value at Z4. In general, where a glass is deformed under fiber drawing tension, a diameter of the glass monotonously decreases. On the other hand, in a method for manufacturing the optical fiber 10, φCL decreases from Z1 to Z4, exhibits a minimum value at Z4 and increases from Z4 to Z5. Then, φCL decreases again in a portion below Z5 and finally becomes a core diameter (φC) of the fiber 10, for example, 27 μm. In other words, inside the fiber drawing furnace 30, the diameter φCL of the core glass decreases and reaches a minimal value and then increases.

Figure 3:
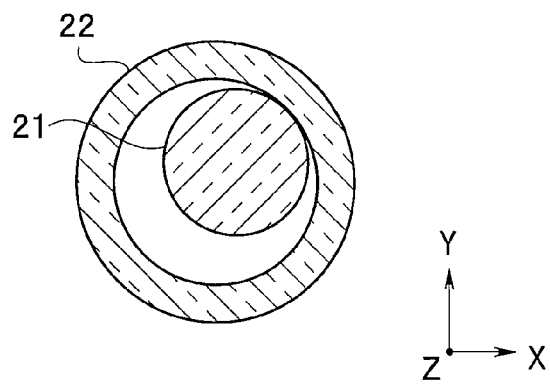
FIG. 3 is a cross-sectional diagram for describing a problem in optical fiber manufacture according to a rod-in-tube method.

Compared with optical fibers for optical communications, optical fibers for endoscopes have a high proportion of the core diameter φC relative to that of a fiber diameter φF. Thus, in a method for manufacturing an optical fiber according to a rod-in-tube method, it is not easy to perform fiber drawing with the core rod 21 accurately arranged in a center of the clad tube 22 inside the fiber drawing furnace, causing a problem in productivity enhancement. In other words, as illustrated in FIG. 3, slight deviation of the core rod 21 from the center of the clad tube 22 may result in the core rod 21 sticking to a part of an inner wall of the clad tube 22 in a phase in which an outer diameter of the core rod 21 is smaller than an inner diameter of the clad tube 22. Consequently, a drawn optical fiber may have a decentered core position, have a non-circular cross sectional shape and/or have variations in fiber diameter.

In particular, optical fibers for endoscopes have a high ratio (φC/φF) of a core diameter φC relative to a fiber diameter φF in order to guide a large amount of light. For example, an optical fiber cannot guide a desired amount of light unless a core diameter φC of the optical fiber is no less than 80% of a fiber diameter φF of the optical fiber. For example, where the fiber diameter φF is 30 μm, the core diameter φC is preferably no less than 24 μm (80%), particularly preferably no less than 27 μm (90%). An upper limit of the core diameter φC is, for example, no more than 95% of the fiber diameter φF, and a core diameter φC that is equal to or below the upper limit enables provision of a clad glass thickness necessary for reflection.

Since optical fibers for endoscopes have a high φC/φF ratio as mentioned above, a ratio (φCT/φCL) of the outer diameter φCL of the core rod 21 relative to an inner diameter φCT of the clad tube 22 is high also at the time of manufacture, and a space (gap) between an outer circumferential face of the core rod and an inner circumferential face of the clad tube is small. Thus, the core rod is easily decentered.

However, in the method for manufacturing an optical fiber according to the present embodiment, a fluidized core glass runs down by gravity and is thereby integrated with a clad glass (clad tube 22). At each of positions below Z4, the diameter of the clad tube 22 further decreases under fiber drawing tension; however, the core glass in the inner portion of the hollow tube (clad tube 22) including the clad glass is in a fluidized state and thus is maintained in a state in which the core glass is evenly charged in the inner portion.

Also, the fiber drawing tension applied from below the fiber drawing furnace 30 is not strongly applied to an upper portion of the core rod 21, that is, a part of Z>Z1 of the core rod 21 since the core rod 21 is in a fluidized state in Z2 to Z5. Therefore, even if the core rod 21 is somewhat deviated from the center of the clad tube 22 in the upper portion of the fiber drawing furnace 30, no large problem occurs.

Thus, the method for manufacturing the optical fiber 10 according to the present embodiment provides high productivity.

As already described, a core glass (core rod 21) entering a fluidized state at a temperature lower than that of a clad glass (clad tube 22) is a requirement for the method for manufacturing the optical fiber 10 according to the present embodiment. In other words, a clad glass and a core glass were selected paying attention to change in a viscosity η1 of the clad glass (clad tube 22) with temperature and change in a viscosity η2 of the core glass (core rod 21) with temperature.

Note that the viscosities η of the glasses were measured by the following methods.
(1) Viscosities at temperature of no more than 900° C.
Fiber elongation method: JIS-R3103 and ASTM-C336
(2) Viscosities at temperature of no less than 900° C.
Using a sphere pull-up viscometer, an imposed load is measured using a balance with a glass regarded as a Newtonian fluid, thereby calculating a viscosity. A sphere pull-up viscometer is a method in which a viscosity is calculated by assigning a load imposed when a platinum sphere is immersed in melt glass and pulled up at a uniform velocity in the Stokes' law.

Here, a glass starts deformation (diameter decrease) under tension where a viscosity η of the glass becomes no more than Log η=6, exhibits noticeable deformation (diameter decrease) under tension where Log η becomes no more than 5, and enters a fluidized state and runs down by gravity where Log η becomes no more than 3.5. Note that "Log" is a common logarithm with base 10.

Here, in order to receive the running-down core glass, the clad glass needs to maintain a predetermined hardness (viscosity). Here, the position Z5 where the clad glass receives the core glass is lower than the position Z2 where the core glass starts running down, and thus, a temperature at Z5 is higher than a temperature at Z2.

Thus, at a temperature at which the viscosity η2 of the core glass becomes Log η2=3.5, the viscosity η2 of the clad glass is preferably Log η1>5.0, particularly preferably Log η1>6.0. Where the viscosity η1 exceeds the aforementioned value, the clad glass can stably receive the running-down core glass. Note that, if the viscosity η1 at a temperature at which the viscosity η2 of the core glass becomes Log η2=3.5 is excessively high, a decrease in diameter of the clad tube 22 after the clad tube 22 receiving the clad glass sharply advances, resulting in unstable fiber drawing, and thus, the viscosity η1 is preferably, for example, Log η1<7.0.

Figure 4:
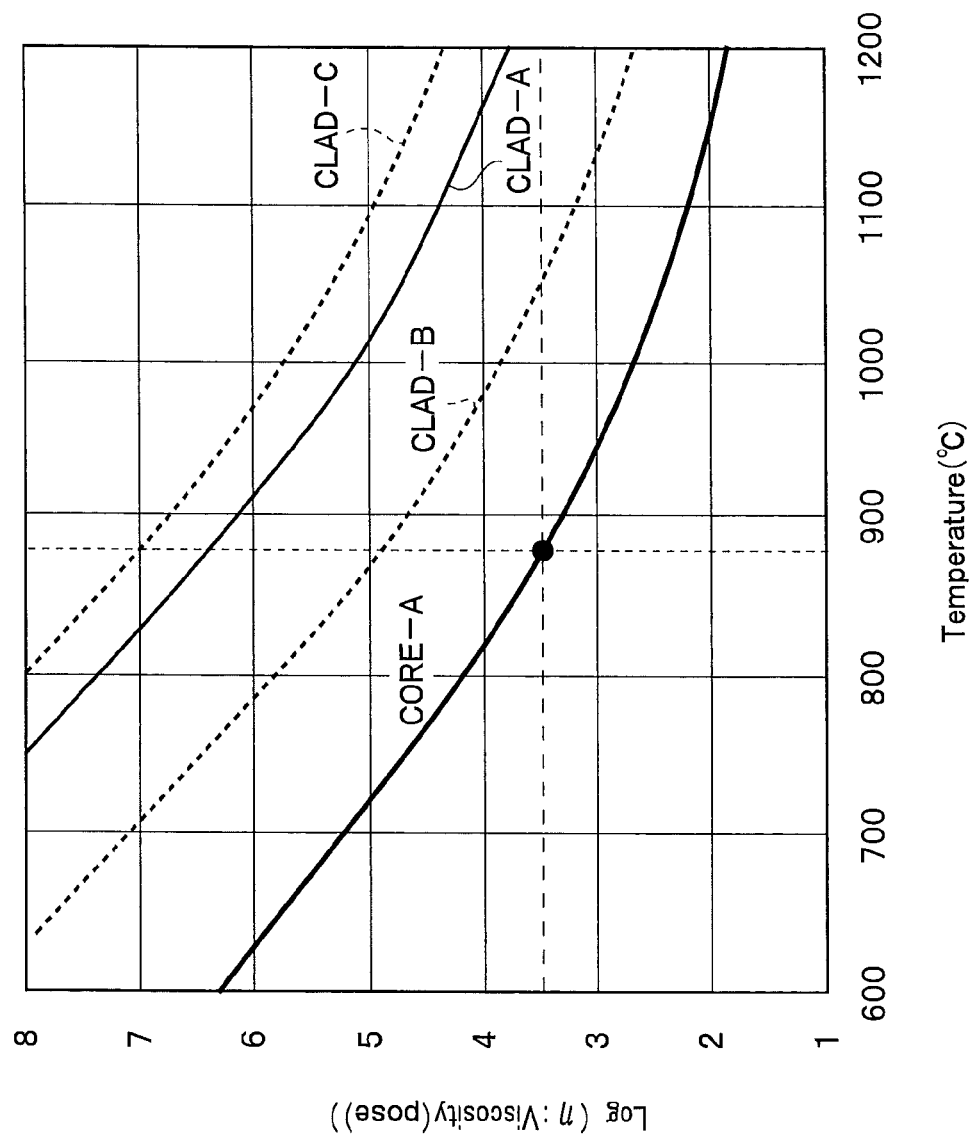
FIG. 4 is a diagram illustrating changes in viscosity of glasses with temperature.

FIG. 4 indicates changes in viscosity of a core glass A (Core-A), a clad glass A (Clad-A), a clad glass B (Clad-B) and a clad glass C (Clad-C) with temperature. A temperature at which the viscosity η2 of the core glass A (Core-A) becomes Log η2=3.5 is 880° C. Then, the clad glass A (Clad-A) whose viscosity η1 at 880° C. is Log η1=6.3 meets the above condition. On the other hand, the clad glass B (Clad-B) whose viscosity η1 at 880° C. is Log η1=5.0 does not meet the above condition, and thus use of the clad glass B (Clad-B) in combination with the core glass A (Core-A) results in a decrease in manufacturing yield of fibers 10 and thus provides poor productivity. Likewise, the clad glass C (Clad-C) whose viscosity η1 at 880° C. is Log η1=7.0 also provides poor productivity.

In other words, a viscosity curve of a clad glass to be combined with the core glass A (Core-A) preferably lies between a viscosity curve of the clad glass B (Clad-B) and a viscosity curve of the clad glass C (Clad-C).

Here, the core glass includes, for example, borosilicate glass or alumino-borosilicate glass as a main component and has a refractive index nd of 1.56 to 1.73. On the other hand, a refractive index nd of the clad glass that includes silica as a main component and also contains, e.g., alkaline components is 1.47 to 1.52. In addition to the above condition, the clad glass is selected with estimation of conditions, such as a refractive index, a difference in thermal expansion coefficient between the clad glass and the core glass, wettability between the core glass and the clad glass and difficulty in mutual component diffusion, according to, for example, Appen's equation.

A viscosity $\eta$ of a glass can be adjusted by adjusting contents of alkaline components. In other words, as the contents of the alkaline components increases, the viscosity $\eta$ at a same temperature decreases.

For example, the clad glass A and the clad glass B are the same in main component, but different from each other in contents of alkaline components. The clad glass A contains 6 mol % Na and 1.5 mol % K. The clad glass B contains 19 mol % Na. Where the effect of Na imposed on the viscosity is "1", that of K is "0.85". In other words, an Na equivalent content in the clad glass A is 7 mol %.

Note that a separately-conducted test indicates that a clad glass meets the viscosity conditions if the clad glass has an alkaline component content of no less than 5 mol % and no more than 17 mol % in Na equivalent.

Here, in the method for manufacturing the optical fiber 10, it is preferable to perform not only temperature management but also time management. In other words, it is preferable to also manage a time period during which a glass, from which a fiber is drawn while the glass moves downward, stays in an region of a predetermined temperature range in the inner portion of the fiber drawing furnace 30.

Here, a time period from a start of deformation and fluidization of a core glass (core rod 21) to fluidization and running-down of the core glass, in other words, a time period required for a viscosity $\eta 2$ of a core glass to decrease from Log $\eta 2$=6.0 to Log $\eta 2$=3.5 is referred to as "first dwell time". Also, a time period from a start of deformation and fluidization of a clad glass (clad tube 22) to achievement of a certain degree of a decrease in diameter of the clad glass (clad tube 22), in other words, a time period required for a viscosity $\eta 1$ of a clad glass to decrease from Log $\eta 1$=6.0 to Log $\eta 1$=5.0 is referred to as "second dwell time".

For example, referring to FIG. 4, a temperature at which the viscosity $\eta 2$ of the core glass A (CORE-A) becomes Log $\eta 2$=6.0 is 620° C., and a temperature at which the viscosity $\eta 2$ of the core glass A (CORE-A) becomes Log $\eta 2$=3.5 is 880° C. In other words, the first dwell time is a time period during which the temperature increases from 620° C. to 880° C.

On the other hand, a temperature at which the viscosity $\eta 1$ of the clad glass A (CLAD-A) becomes Log $\eta 1$=6.0 is 910° C. and a temperature at which the viscosity $\eta 1$ of the clad glass A (CLAD-A) becomes Log $\eta 1$=5.0 is 1010° C. In other words, the second dwell time is a time period during which the temperature increases from 910° C. to 1010° C.

Figure 5:
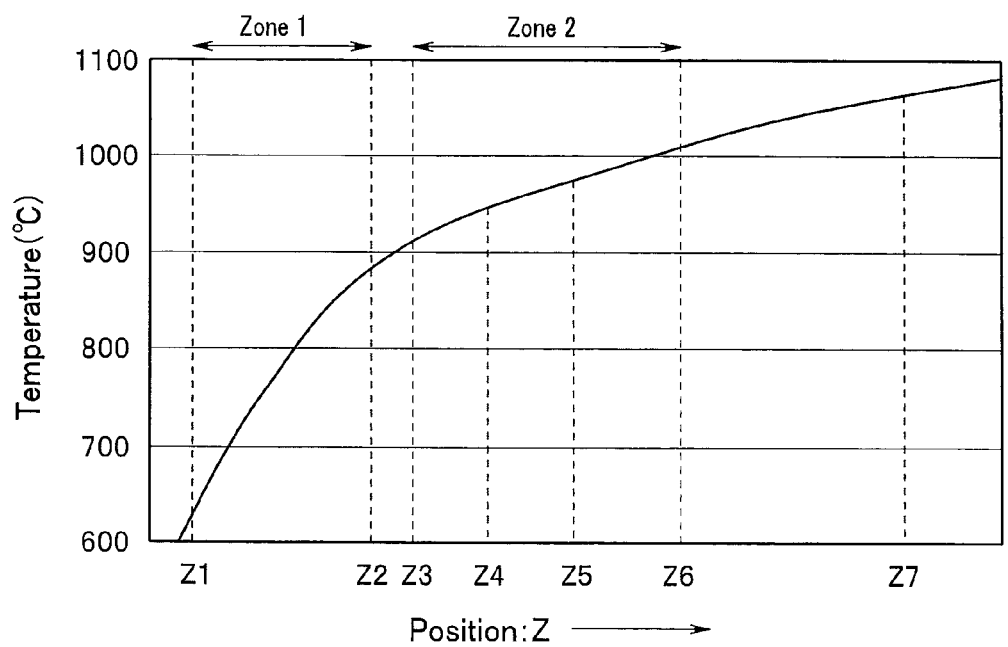
FIG. 5 is a diagram illustrating a temperature distribution in a fiber drawing furnace according to an embodiment.

Here, FIG. 5 illustrates a temperature distribution in the fiber drawing furnace 30. In this case, the first dwell time is a dwell time for a first temperature range of 620° C. to 880° C., and the second dwell time is a dwell time for a second temperature range of 910° C. to 1010° C.

Each of a dwell time during which the core glass stays in the first temperature range and a dwell time during which the clad glass stays in the second temperature range is more preferably a time period (in minutes) no less than 0.15 times a value of a core outer diameter represented in millimeters for stable manufacture. Note that, although the core outer diameter (core diameter $\phi$CL) varies in the inner portion of the fiber drawing furnace 30, an initial outer diameter of a core glass before fiber drawing processing is used for the dwell time calculation.

For example, if the core outer diameter is 30 mm, each of the two dwell times is more preferably no less than (30×0.15) minutes, that is, no less than 4.5 minutes. Note that the dwell times are each determined based on the fiber drawing speed and the region length. For example, if a length of a temperature region is 20 mm, it is only necessary that the fiber drawing speed in the temperature region be no more than 4 mm/minutes.

Furthermore, for productivity enhancement, each of the dwell times for the first temperature range and the second temperature range is preferably, for example, a time period (in minutes) no more than twice a value of the core outer diameter represented in millimeters. For example, if the core outer diameter is 30 mm, each of the two dwell times is no more than (30×2) minutes, that is, no more than 60 minutes.

Note that, as illustrated in FIG. 5, in the case of a combination of the core glass A (CORE-A) and the clad glass A (CLAD-A), there is no overlapping region where the first temperature range and the second temperature range overlap; however, there may be such overlapping region. In other words, the temperature at which the viscosity $\eta 2$ of the core glass becomes Log $\eta 2$=3.5 may be lower than the temperature at which the viscosity $\eta 1$ of the clad glass becomes Log $\eta 1$=6.0.

<Optical Fiber Configuration>

As described above, in the optical fiber 10 for an endoscope, which is inserted into the insertion portion of the endoscope and guides light, the viscosity $\eta 1$ of the clad glass at a temperature at which the viscosity $\eta 2$ of the core glass becomes Log $\eta 2$=3.5 is 5.0<Log $\eta 1$<7.0. Also, in the optical fiber 10, the core diameter is no less than 80% and no more than 95% of the fiber diameter. The optical fiber 10 is manufactured according to a rod-in-tube method using an upright fiber drawing furnace.

Since the optical fiber 10 provides good productivity, the optical fiber 10 can be manufactured at low costs.

<Endoscope Configuration>

Figure 6:
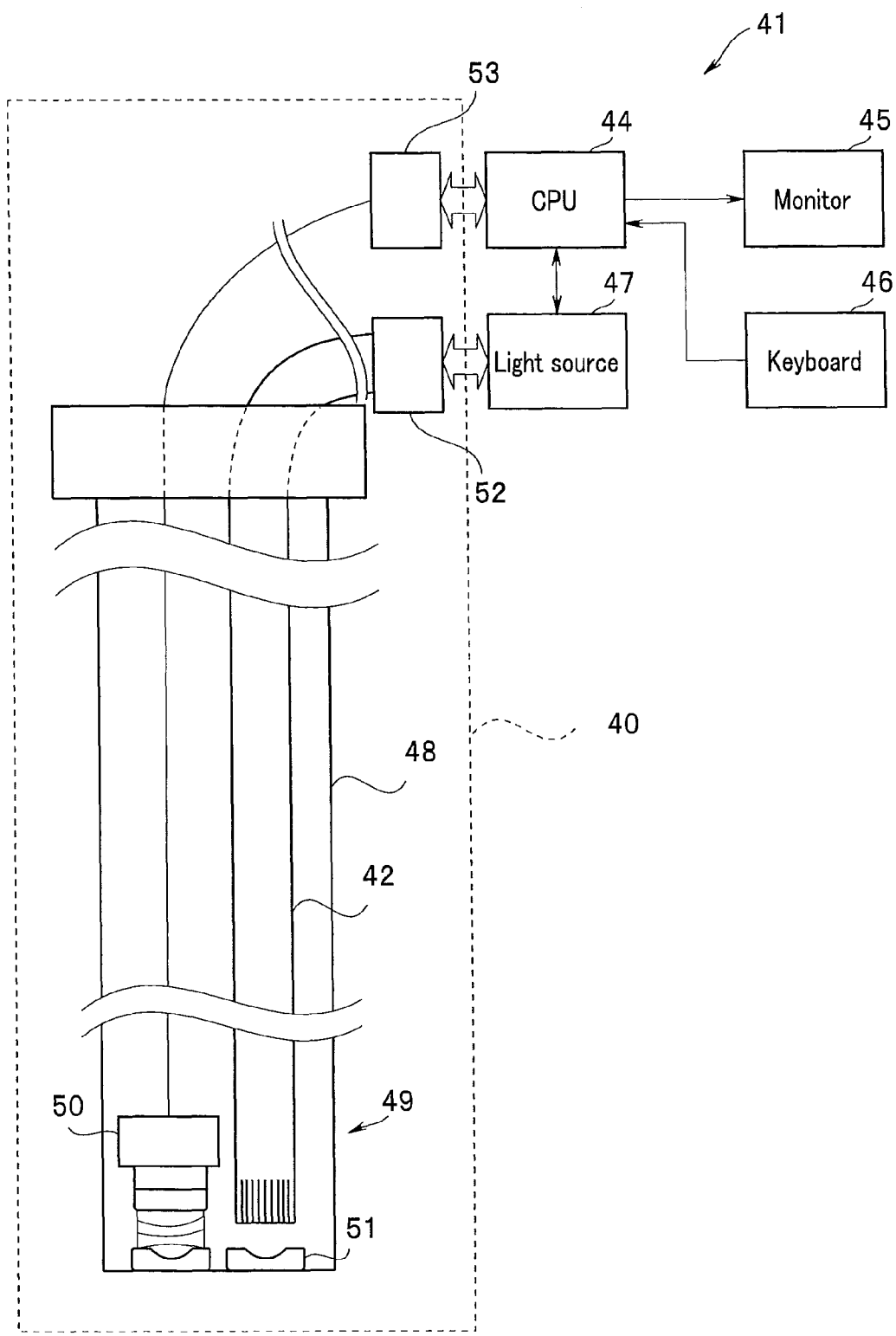
FIG. 6 is a configuration diagram for describing a configuration of an endoscope according to an embodiment.

Next, an endoscope 40 including optical fibers 10 will briefly be described with reference to FIG. 6.

An endoscope system 41 including the endoscope 40 includes a CPU 44, which is a processor that processes an image signal, a monitor 45 that displays an endoscopic image, an input section such as a keyboard 46 for a user to set, e.g., use conditions, and a light source apparatus 47.

The endoscope 40 is an electronic endoscope including an insertion portion 48 that includes, in a distal end portion 49 thereof, an image pickup section 50 that picks up a color endoscopic image and an illumination optical system 51, a light guide 42 inserted into an inner portion of the insertion portion 48, the light guide 42 guiding illuminating light from a light source apparatus 47 connected thereto via a light guide connector 52 on the proximal end portion side thereof to the illumination optical system 51, and an electronic connector 53 connecting the image pickup section 50 including, e.g., a CCD and the CPU 44.

The light guide 42 includes, for example, 2800 optical fibers 10 charged in a silicone tube, each of the optical fibers 10 having a diameter of 30.0 μm, and has a diameter of 1.8 mm and a length of 1 m.

The endoscope 40 includes the optical fibers 10, which provide good productivity, and thus, provides good productivity and can be manufactured at low costs.

Note that, although the above description has been provided in terms of the optical fibers 10 for a light guide for illumination, the light guide guiding illuminating light from a proximal end portion to the distal end portion 49 of the insertion portion 48, the embodiment of the present invention provides effects similar to those of the optical fiber 10 even in the case of an optical fiber for a light guide for image pickup, the light guide guiding light of an object image received by an image pickup optical system in the distal end portion 49 to the proximal end portion side. In other words, e.g., the optical fiber 10 and the method for manufacturing the optical fiber 10 according to the embodiment have various uses for endoscopes.

Also, the present invention is not limited to the above-described embodiment and the like, various modifications and alterations are possible without departing from the spirit of the present invention.

What is claimed is:

1. A method for manufacturing an optical fiber that is inserted into an insertion portion of an endoscope and guides light,
   wherein in an inner portion of an upright fiber drawing furnace used in an rod-in-tube method, in an inner portion of a hollow clad tube including a clad glass having a viscosity $\eta 1$ of $5.0 < \text{Log } \eta 1 < 7.0$ at a temperature at which a viscosity $\eta 2$ of a core glass becomes Log $\eta 2 = 3.5$, the core glass in a fluidized state runs down by gravity, whereby the core glass and the clad glass are integrated.

2. The method for manufacturing an optical fiber according to claim 1, wherein a core diameter of the optical fiber is no less than 80% and no more than 98% of a fiber diameter of the optical fiber.

3. The method for manufacturing an optical fiber according to claim 2, wherein in the inner portion of the fiber drawing furnace, a diameter of a core rod including the core glass increases after the diameter reaches a minimal value.

4. The method for manufacturing an optical fiber according to claim 1, wherein in the inner portion of the fiber drawing furnace, a dwell time during which the core glass stays in a first temperature range in which the viscosity $\eta 2$ of the core glass decreases from Log $\eta 2 = 6.0$ to Log $\eta 2 = 3.5$ is a time period (in minutes) no less than 0.15 times a value of an initial outer diameter of the core glass represented in millimeters, and a dwell time during which the clad glass stays in a second temperature range in which the viscosity $\eta 1$ of the clad glass decreases from Log $\eta 1 = 6.0$ to Log $\eta 1 = 5.0$ is a time period (in minutes) no less than 0.15 times the value of the outer diameter represented in millimeters.

5. An optical fiber that is inserted into an insertion portion of an endoscope and guides light,
   wherein a viscosity $\eta 1$ of a clad glass at a temperature at which a viscosity $\eta 2$ of a core glass becomes Log $\eta 2 = 3.5$ is $5.0 < \text{Log } \eta 1 < 7.0$.

6. The optical fiber according to claim 5, wherein a core diameter is no less than 80% and no more than 98% of a fiber diameter.

7. The optical fiber according to claim 6, wherein the optical fiber is manufactured according to a rod-in-tube method using an upright fiber drawing furnace.

8. An endoscope comprising an optical fiber that is inserted into an insertion portion and guides light, wherein a viscosity $\eta 1$ of a clad glass at a temperature at which a viscosity $\eta 2$ of a core glass becomes Log $\eta 2 = 3.5$ is $5.0 < \text{Log } \eta 1 < 7.0$.

* * * * *